United States Patent [19]

St. George et al.

[11] Patent Number: 5,763,634

[45] Date of Patent: *Jun. 9, 1998

[54] PROCESS FOR THE PREPARATION OF FERRIC CHELATE SOLUTIONS OF ALKALI METAL POLYAMINO SUCCINIC ACIDS

[75] Inventors: George M. St. George, Lake Jackson; David A. Wilson, Richwood; S. Bennett Willis, Lake Jackson, all of Tex.

[73] Assignee: The dow Chemical Company, Midland, Mich.

[*] Notice: The term of this patent shall not extend beyond the expiration date of Pat. No. 5,717,123.

[21] Appl. No.: 767,611

[22] Filed: Dec. 17, 1996

Related U.S. Application Data

[63] Continuation-in-part of Ser. No. 711,624, Sep. 12, 1996, Pat. No. 5,717,123.

[51] Int. Cl.⁶ .................................................. C07F 15/02
[52] U.S. Cl. ................................................... 556/148
[58] Field of Search ...................................... 556/148

[56] References Cited

U.S. PATENT DOCUMENTS

| | | | |
|---|---|---|---|
| 5,569,443 | 10/1996 | Wilson et al. | 423/576.6 |
| 5,582,958 | 12/1996 | Buchanan et al. | 430/393 |

*Primary Examiner*—Porfirio Nazario-Gonzalez

[57] ABSTRACT

A method for the preparation of concentrated, stable iron chelate solutions of alkali metal polyamino succinic acids is disclosed. The method involves the co-feeding of an alkaline alkali-metal succinate solution and a ferric salt solution into a vessel.

35 Claims, No Drawings

PROCESS FOR THE PREPARATION OF FERRIC CHELATE SOLUTIONS OF ALKALI METAL POLYAMINO SUCCINIC ACIDS

This application is a Continuation-In-Part of the application Ser. No. 08/711,624, filed Sep. 12, 1996, now U.S. Pat. No. 5,717,123.

This invention relates to a novel process for producing iron complexes of polyamino succinic acid compounds.

BACKGROUND OF THE INVENTION

Chelants or chelating agents are compounds which form coordinate covalent bonds with a metal ion to form chelates. Chelates are coordination compounds in which a central metal atom is bonded to two or more other atoms in at least one other molecule (ligand) such that at least one heterocyclic ring is formed with the metal atom as part of each ring.

Chelants are used in a variety of applications including food processing, soaps, detergents, cleaning products, personal care products, pharmaceuticals, pulp and paper processing, water treatment, metalworking and metal plating solutions, textile processing solutions, fertilizers, animal feeds, herbicides, rubber and polymer chemistry, photofinishing, and oil field chemistry. Some of these activities result in chelants entering the environment. For instance, agricultural uses or detergent uses may result in measurable quantities of the chelants being present in water. It is, therefore, desirable that chelants degrade after use. Of particular interest are chelating agents which are biodegradable, that is chelating agents which are susceptible to degradation by microorganisms.

In the bleaching stage of photographic materials, a particularly important class of bleaching agents are the aminopolycarboxylic acid bleaching agents, such as an ammonium or alkali metal salt of a ferric complex of ethylenediaminetetraacetic acid (EDTA). Ferric complex salts of propylenediaminetetraacetic acid (PDTA) having a higher bleaching power than EDTA have also been widely used as bleaching agents.

Although chelants or chelating agents, such as EDTA and PDTA, are effective in the bleaching step of photographic materials, there is interest in the photography industry to obtain chelants for use in the bleaching process which biodegrade more rapidly than EDTA and PDTA. Finding suitable chelants for use in photography, which are more biodegradable than what is commonly used, is difficult as the chelant must be able to chelate iron as well as have the proper redox ability.

There have been several chelating agents reported to be biodegradable for use in a bleaching stage for photographic materials. EP patent application 0532003, published Mar. 17, 1993, EP application 0584665 published Mar. 2, 1994, and EP Patent Application 0567126, published Oct. 27, 1993, all disclose diamine compounds which are useful in processing silver halide light-sensitive photographic material. These compounds are reported to have improved biodegradability and safety. EP Patent Application 0599620, published Jun. 1, 1994, further discloses monoamine and polyamine compounds which can be used in processing silver halide-photographic light-sensitive material and are reported to have good degradation characteristics. The use of polyamino disuccinic acid chelating compounds in photographic bleach and bleach fixing solutions is further disclosed in WO 94/28464 published Dec. 8, 1994. Although the use of iron complexes of polyamino disuccinates is disclosed, there is no description of how to make concentrated solutions of these complexes.

For use of ferric polyamino disuccinic acid complexes in applications, such as photographic bleaching, where the complex is diluted during formulation, it is desirable for economical and practical process conditions, that the amount of iron in a stable solution with the chelating agent be as great as possible.

SUMMARY OF THE INVENTION

The present invention is to a process for producing a ferric chelate of a polyamino disuccinic acid comprising adding an alkali metal salt of the polyamino disuccinic acid to an aqueous solution of a ferric salt under conditions to produce a stable iron chelate solution of greater than one percent by weight iron.

In another aspect the invention is to a process for producing a ferric chelate of a polyamino disuccinic acid and polyamino monosuccinic acid comprising adding an alkali metal salt of a mixture of a polyamino disuccinic acid and a polyamino monosuccinic acid to an acidic solution of a ferric salt under conditions to produce a stable iron chelate solution of greater than one percent by weight iron.

In another aspect the invention is to a process for producing a ferric chelate of a polyamino disuccinic acid comprising adding simultaneously to a vessel a solution of an alkali metal salt of the polyamino disuccinic acid and a solution of a ferric salt under conditions to produce a stable iron chelate solution wherein the final iron chelate solution is greater than one percent by weight iron.

In still another aspect, the invention is to a process for producing a ferric chelate of a polyamino disuccinic acid and polyamino monosuccinic acid comprising adding simultaneously to a vessel a solution of alkali metal salts of a mixture of a polyamino disuccinic acid and a polyamino monosuccinic acid and a ferric salt solution under conditions to produce a stable iron chelate solution wherein the final chelate solution is greater than one percent by weight iron.

DETAILED DESCRIPTION OF THE INVENTION

It has been found that the procedure by which soluble ferric salts are mixed with an alkaline alkali-metal polyamino dissuccinic solution acid, unexpectedly has a profound effect on obtaining a concentrated, stable iron chelate solution. By the process of the present invention a concentrated stable iron chelate solution is obtained. The concentrated iron chelate solutions allow for a lower cost of production and shipment of a concentrated product which can then be diluted and/or formulated for use. concentrated iron chelate solution means a ferric chelate solution containing greater than one percent by weight iron. Depending on the end use application, the iron concentration, by weight, is generally between 1.1 and 5 percent. Preferably the weight percent of iron is from 2 to 5 percent. For use in photographic bleaching and other photographic processes, it is preferred that the iron chelate solution contains from 2 to 5 percent by weight iron, which is then diluted during formulation. A stable solution as used herein means a chelate solution that contains no visible oxides/hydroxides of iron.

The process of the present invention requires the addition of a water-soluble salt, notably an alkali metal salt, ammonium salt, or alkylammonium salt of a polyamino disuccinic acid to an aqueous ferric salt solution. The alkali metal salts can involve one or a mixture of alkali metals. Based on the production process for the polyamino disuccinic acid, the preferred alkali metal is sodium or potassium. Preferred ferric salts which are soluble in water include ferric halide salts, and the nitrate, acetate and sulfate salts. The preferred salt is ferric nitrate. The addition of the polyamino disuccinic acid occurs under mixing conditions. Mixing can be achieved by conventional means used in chemical reactors.

The polyamino disuccinic acid is added to the ferric salt solution in an approximate molar ratio of one to one (ligand to iron). Higher ligand to iron molar ratios may be used to give stable iron chelate solutions. Due to economical considerations with respect to the cost of the starting materials, additional ferric salt can be added to systems containing excess chelant to produce a molar ratio of ligand to iron in the range of from about 1.05:1 to about 1.3:1. Preferably the molar ratio of polyamino disuccinic acid to iron is in slight excess of the 1:1 ratio, such as about 1.05:1.

The initial concentration of iron in solution and the concentration of the polyamino succinic acid solution are generally chosen to give final iron concentrations of greater than one percent by weight. Thus under conditions to produce an iron chelate solution of greater than one percent iron means that the concentration of iron initially present, with the dilution of chelant in slight molar excess, will give a final product greater than one percent iron by weight. Calculations to determine these initial concentrations required are within the ordinary skill of one in the art.

By the inherent nature of the compounds, the pH of the ferric salt solution will be acidic and the pH of the alkali-metal polyamino disuccinic acid compound will be alkaline. Generally the pH of the alkali-metal polyamino disuccinic acid solution will be from 8 to 14. Preferably the pH of the polyamino disuccinic acid solution will be from 9 to 13. The pH of the ferric salt solution will generally be from less than 0 to 4. The pH of the alkali-metal polyamino disuccinic acid solution is generally chosen so that upon addition of the polyamino disuccinic acid to the ferric salt solution, the final pH of the product will be from 3 to 8, and preferably from 4 to 7. If needed the pH can be adjusted to the desired pH range by the addition of acid or base.

The reaction temperature can range from about 5 to about 110° C. and is preferably at ambient conditions (5°–30° C.). After the addition of the polyamino succinic acid, when the concentration of starting materials is high, a fluid slurry-type material may be obtained which can be heated to give a solution. When heating is required, this increases the processing time and energy cost. Generally when heat is applied, the temperature of the solution is held below 100° C. as excess heating can lead to degradation of the ligand.

When the polyamino disuccinic acid is added to the ferric salt solution according to the above described procedure, the reaction mixture goes through a thick slurry stage which dissolves as the molar ratio of chelating agent to iron approaches one. In an alternative preferred process, it has been found that the formation of this thick slurry can be substantially avoided by simultaneously feeding into a vessel the polyamino disuccinic acid and ferric salt solution. When operating under normal manufacturing conditions, the polyamino disuccinic acid and ferric salt solutions are added to a vessel containing a "heel", that is, ferric chelate solution remaining in the vessel from a prior reaction mix. Alternatively, the reaction vessel may contain a fluid, such as water. The term vessel open ended containers such as a pipe into which the components are co-fed.

When the polyamino disuccinic acid and ferric salt are co-fed into a vessel, the concentration of the feed streams are selected to give a final iron concentration of greater than one percent by weight with the molar ratio of chelating agent to iron as previously described. Generally the polyamino disuccinic acid and ferric salt are simultaneously added to a vessel at about a one to one molar ratio, however; higher ligand to iron molar ratios can be used In contrast to the processes of the present invention, when a ferric salt solution is added to a solution of a polyamino disuccinic acid under ambient reaction temperatures, the reaction mixture forms insoluble iron oxides/hydroxides when the iron concentration is nominally greater than about one percent by weight. Some of the formed insoluble iron oxides/hydroxides can be solubilized upon prolonged heating, that is 70°–110° C. for greater than 30 minutes.

Polyamino disuccinic acids are compounds having at least two nitrogen atoms wherein two of the nitrogen atoms are bonded to succinic acid moieties. Due to the commercial availability of the amine, the compounds preferably have no more than about 10 nitrogen atoms, more preferably no more than about 6, most preferably 2 nitrogen atoms. Preferably, the succinic acid groups are on terminal nitrogen atoms. Remaining bonds on nitrogens having a succinic acid group are preferably filled by hydrogens or alkyl or alkylene groups (linear, branched or cyclic including cyclic structures joining more than one nitrogen atom or more than one bond of a single nitrogen atom, preferably linear) or such groups having ether or thioether linkages, all of preferably from 1 to about 1 0 carbon atoms, more preferably from 1 to about 6, most preferably from 1 to about 3 carbon atoms, but most preferably hydrogen. The nitrogen atoms are linked by alkylene groups, preferably each of from about 2 to about 12 carbon atoms, more preferably from about 2 to about 10 carbon atoms, even more preferably from about 2 to about 8, most preferably from about 2 to about 6 carbon atoms. The polyamino disuccinic acid compound preferably has at least about 10 carbon atoms and preferably has at most about 50, more preferably at most about 40, most preferably at most about 30 carbon atoms. The term "succinic acid" as used herein means the acid and salts thereof; the salts include metal cation (e.g. potassium, sodium) and ammonium or amine salts.

Polyamino disuccinic acids useful in the practice of the invention are unsubstituted (preferably) or inertly substituted, that is substituted with groups that do not undesirably interfere with the activity of the polyamino disuccinic acid in a selected application, particularly photographic uses. Such inert substitutents include alkyl groups (preferably of from 1 to about 6 carbon atoms); aryl groups including arylalkyl and alkylaryl groups (preferably of from 6 to about 12 carbon atoms). The atoms of the polyamino disuccinic acid compounds may be substituted with from 0 to 12 atoms other than carbon selected from the group consisting of oxygen, sulfur, phosphorus, nitrogen, hydrogen and various combination of these elements.

Preferred polyamino disuccinic acids include ethylenediamine-N,N'-disuccinic acid, diethylenetriamine-N,N"-disuccinic acid, triethylenetetraamine N,N'"-disuccinic acid, 1,6-hexamethylenediamine -N,N'-disuccinic acid, tetraethylenepentamine-N,N""-disuccinic acid, 2-hydroxypropylene-1,3-diamine N,N'-disuccinic acid, 1,2-propylenediamine N,N'-disuccinic acid, 1,3-propylenediamine-N,N'-disuccinic acid, cis-cyclohexanediamine -N,N'-disuccinic acid, trans-cyclohexanediamine-N,N'-disuccinic acid, and ethylenebis (oxyethylenenitrilo)-N,N'-disuccinic acid.

Such polyamino disuccinic acids can be prepared, for instance, by the process disclosed by Kezerian et al. in U.S. Pat. No. 3,158,635 which is incorporated herein by reference in its entirety. Kezerian et al disclose reacting maleic anhydride (or ester or salt) with a polyamine corresponding to the desired polyamino disuccinic acid under alkaline conditions. The reaction yields a number of optical isomers, for example, the reaction of ethylenediamine with maleic anhydride yields a mixture of three optical isomers [R,R], [S,S] and [S,R] ethylenediamine disuccinic acid (EDDS) because there are two asymmetric carbon atoms in ethylenediamine disuccinic acid. These mixtures are used as mixtures or alternatively separated by means within the state of the art to obtain the desired isomer(s). Alternatively, [S,S] isomers are prepared by reaction of such acids as L-aspartic acid with such compounds as 1,2-dibromoethane as described by Neal and Rose, "Stereospecific Ligands and Their Complexes. A Cobalt III Complex of Ethylenediaminedisuccinic Acid", *Inorganic Chemistry*, v. 7, (1968), pp. 2405–2412.

The polyamino disuccinic acid which is added to the ferric salt solution can contain other metal chelating compounds. An example of other chelating agents which can be present are polyamino monosuccinic acids which may be formed during the synthesis of the polyamino disuccinic acid compounds. When a polyamino monosuccinic acid is also present, it is preferred that the polyamino substituent of the polyamino disuccinic acid and polyamino monosuccinic acid are the same. Thus by way of example, if the polyamino dissuccinic acid is ethylenediamine-N,N'-disuccinic acid, the polyamino monosuccinic acid is ethylenediamine monosuccinic acid.

The ferric chelates formed by the present process are particularly useful in photographic processing solutions having bleaching ability, which solutions include both bleaching solutions and bleach-fixing solutions.

The invention will be further clarified by a consideration of the following examples, which are intended to be purely exemplary of the present invention. All percents are percent by weight unless otherwise indicated.

COMPARATIVE EXAMPLE A

Into a beaker containing a magnetic stirrer bar were added 9.12 grams of a meso-racemic mixture of ethylenediamine-N,N'-disuccinic acid (98%) and 21.61 grams of deionized water. The slurry was cooled in an ice-water bath and with good agitation, 19.53 grams of 25% NaOH solution was added. The reaction solution (pH=12.9) was removed from the ice-water bath and 14.6 grams of a ferric nitrate solution containing 11.1% iron was added over a 5 minute period to the stirred solution in order to give a nominal concentration of 2.5% iron and a ligand to iron molar ratio of 1.05. The reaction mixture was stirred for 2 hours at room temperature and then bottled (pH=4.0). This procedure resulted in a product that contained insoluble oxides/hydroxides of iron.

COMPARATIVE EXAMPLE B

Into a beaker containing a magnetic stirrer bar were added 11.24 grams of a meso-racemic mixture of ethylenediamine-N,N'-disuccinic acid (98%) and 20.80 grams of deionized water. The mixture was cooled in an ice-water bath and with good agitation, 12.06 grams of 50% NaOH solution was added. The temperature was maintained at less than 15° C. during the addition. With continued stirring and cooling, 24.84 grams of a ferric chloride solution containing 6.52% iron was added dropwise over a 25 minute period in order to give a nominal concentration of 2.35% iron and a ligand to iron molar ratio of 1.3. The temperature was maintained at 10°–11° C. during the addition of the ferric chloride solution. The reaction mixture was stirred for 3 hours at room temperature at which time the reaction mixture consisted of a very thick slurry of brown looking solids. Approximately 2.3 grams of a 28% ammonia solution were added to obtain a pH of 7.9 and stirring was continued for 4 hours at room temperature. This procedure resulted in a product that contained insoluble iron oxides/hydroxides.

COMPARATIVE EXAMPLE C

Into a beaker containing a magnetic stirrer bar were added 24.97 grams of deionized water and 25.04 grams of a solution containing a mixture of optical isomers consisting of 37.8% tetrasodium ethylenediamine-N,N'-disuccinate and 5.0% disodium ethylenediamine-N-monosuccinate. The chelant solution was prepared by the reaction of ethylenediamine with maleic acid and NaOH. The reaction solution (pH=12.6) was stirred and 14.6 grams of ferric nitrate solution (11.1% iron) was added in order to give a nominal concentration of 2.5% iron and a total ligand to iron molar ratio of 1.05. The mixture was stirred for 4 hours at room temperature. The product (pH=3.9) had insoluble iron oxides/hydroxides present.

COMPARATIVE EXAMPLES D, E, F & G

The procedure of Comparative Example C was used with varying amounts of water in order to give products with a nominal iron concentration of 2.0%, 1.5%, 1.25% and 1.0% iron. Examples D, E, F and G respectively. As in Comparative Example C, the total chelant to iron molar ratio was 1.05 and the mixtures were stirred for 4 hours at room temperature. At the end of this time, the 2.0%, 1.5% and 1.25% iron products had insoluble iron oxides/hydroxides present. The product prepared at 1.0% iron resulted in a stable iron chelate solution that did not have insoluble oxides/hydroxides.

COMPARATIVE EXAMPLE H

Into a beaker containing a magnetic stirrer bar were added 15.0 grams of deionized water and 25.02 grams of a solution containing a mixture of optical isomers consisting of 37.8% tetrasodium ethylenediamine-N,N'-disuccinate and 5.0% disodium ethylenediamine-N-monosuccinate. The reaction solution (pH=12.7) was stirred and 24.84 grams of a ferric chloride solution containing 6.52% iron was added in order to give a nominal concentration of 2.5% iron and a ligand to iron molar ratio of 1.05. The reaction mixture was stirred for 2 hours at room temperature. The final product (pH=3.9) had insoluble iron oxides/hydroxides present.

COMPARATIVE EXAMPLE I

The technique used to prepare the product of Example F was used except that a ligand to iron molar ratio of 1.25 was used instead of 1.05. The final product had insoluble oxides/hydroxides of iron present.

COMPARATIVE EXAMPLE J

Into a beaker containing a magnetic stirrer bar were added 18.0 grams of deionized water and 25.0 grams of a solution containing a mixture of optical isomers consisting of 37.8% tetrasodium ethylenediamine-N,N'-disuccinate and 5.0% disodium ethylenediamine-N-monosuccinate. With stirring, 2.1 grams of a 37% hydrochloric acid solution was added to obtain a pH of 9.5 followed by the addition of 14.6 grams of a ferric nitrate solution (11.1% iron). The reaction mixture was stirred for 2 hours at room temperature at which point a slurry of tan-colored solids was obtained (pH=2.6). Aqueous ammonia solution was then added to adjust the pH to 7 and achieve a 2.5% nominal iron product at a 1.05 total chelant to iron molar ratio. The reaction mixture was stirred for an additional 4.5 hours and bottled. The product contained some insoluble iron oxides/hydroxides, although visually less than the previously described products at comparable iron concentrations.

COMPARATIVE EXAMPLE K

A 100-ml beaker was charged with 28.0 g of the chelant solution described in Example 7. The solution was vigorously stirred with a magnetic stirring bar while 15 g of the ferric nitrate solution described in Example 7 diluted with 12 g deionized water was added dropwise over a period of twenty minutes. The resulting dark brown slurry was heated to 90° C. and kept there for one hour. After cooling to 40° C., the mixture was filtered, removing about 0.3 g of a brown solid. 46 g of iron chelate solution was recovered, containing 3.3% Fe by weight.

COMPARATIVE EXAMPLE L

A beaker containing a magnetic stir bar was charged with 50 g of a "heel" from a previous run (3.4% iron). To this heel was added dropwise 362 g of a chelant solution (37.8% tetrasodium ethylenediamine-N,N'-disuccinate, (0.360 mole), and 5.1% disodium ethylenediamine-N-monosuccinate (0.083 mole)). The final pH of this solution was 12.1. No precipitation was observed upon standing overnight. To this solution was added dropwise, 195 g of the ferric nitrate solution described in Example 7 diluted with 177 g of deionized water. Copious precipitation was observed upon the addition of the ferric nitrate solution. The resulting slurry was heated at 95° C. for two hours, cooled to 55° C., and filtered through a 0.45 micron filter removing 8 g of brown solids. The filtrate weighted 656 g and contained 3.08% iron by weight, accounting for 82% of the total iron charged.

EXAMPLE 1

Into a beaker containing a magnetic stirrer bar were added 18.5 grams of deionized water and 14.6 grams of ferric nitrate solution (11.1% iron). With good agitation, 28.7 grams of a 40% aqueous solution of the tetrasodium salt of meso-racemic ethylenediamine-N,N'-disuccinic acid was added over a 5 minute period. The reaction mixture goes through a thick slurry stage and then dissolves as the alkaline succinate solution is added. The reaction mixture was stirred at room temperature for 2 hours to give a stable 2.5% iron chelate solution (pH=5.4) containing no observable insoluble iron oxides/hydroxides. The final molar ratio of chelant to iron was 1.04.

EXAMPLE 2

Into a beaker containing a magnetic stirrer bar were added 21.2 grams of deionized water and 14.6 grams of ferric nitrate solution (11.1% iron). With good agitation, 34.0 grams of a 40% solution of the tetrapotassium salt of meso-racemic ethylenediamine-N,N'-disuccinic acid was added over a 5 minute period. As in the above Example 1, the reaction proceeds through a thick slurry stage, followed by the dissolution of the reaction mixture. The reaction mixture was stirred at room temperature for 2 hours to give a stable 2.3% iron chelate solution (pH=5.8) containing no observable insoluble iron oxides/hydroxides. The final molar ratio of chelant/iron was 1.05.

EXAMPLE 3

Into a beaker containing a magnetic stirrer bar were added 87.6 grams of ferric nitrate solution (11.1 % iron) and 150.1 grams of deionized water. With good agitation, 150.0 grams of a solution containing a mixture of optical isomers consisting of 37.8% tetrasodium ethylenediamine-N,N'-disuccinate and 5.0% disodium ethylenediamine-N-monosuccinate was added over a 20 minute period. This chelant solution was prepared by the reaction of ethylenediamine with maleic acid and NaOH. The reaction mixture was stirred for 2 hours to give a 2.5% iron chelate solution (pH=4.6) containing no observable insoluble iron oxides/hydroxides. The total ligand to iron molar ratio was 1.05.

EXAMPLE 4

Into a beaker containing a magnetic stirrer bar were added 87.6 grams of ferric nitrate solution (11.1 % iron) and 109.1 grams of deionized water. With good agitation, 192.0 grams of a solution containing a mixture of optical isomers consisting of 37.8% tetrasodium ethylenediamine-N,N'-disuccinate and 5.0% disodium ethylenediamine-N-monosuccinate was added over a 45 minute period. The solution (pH=6.5) was stirred for approximately 1 hour and then 24.0 grams of the ferric nitrate solution was added over a 10 minute period. The reaction mixture was stirred until complete dissolution was obtained. The procedure resulted in the preparation of a stable 3.0% iron chelate solution (pH=4.7) at a total chelant to iron molar ratio of 1.05.

EXAMPLE 5

Into a beaker containing a magnetic stirrer bar were added 30.0 grams of deionized water and 24.84 grams of ferric chloride solution (6.52% iron). With good agitation, 26.2 grams of a solution containing a mixture of optical isomers consisting of 37.8% tetrasodium ethylenediamine-N,N'-disuccinate and 5.0% disodium ethylenediamine-N-monosuccinate was added over a 10 minute period. As in the above examples, the reaction proceeds through a thick slurry stage followed by the dissolution of the reaction mixture. The reaction mixture was stirred at room temperature for 5 hours at which time a stable 2.0% iron chelate solution was obtained which did not contain any observable insoluble iron oxides/hydroxides. The molar ratio of total chelant to iron was 1.1.

EXAMPLE 6

A beaker containing a magnetic stir bar was charged with 180 g of ferric nitrate solution (11.1 % Fe, 0.358 mole) and 100 g of deionized water. With vigorous stirring, 310 g of chelant solution (39.3% tetrasodium ethylenediamine-N,N'-disuccinate, 0.320 mole, and 5.17% disodium ethylenediamine-N-monosuccinate, 0.073 mole) was added over a period of ten minutes. The mixture passed through a thick slurry phase, giving a fine slurry when the addition was complete. The mixture was warmed to 90° C. over half an hour and held there another half hour. The resulting solution was cooled to 50° C. and filtered through a 0.45 micron nylon filter, removing about 0.1 g of insoluble material. 572 g of solution was recovered, containing 3.24% Fe by weight (ICP analysis). The total ligand-to-metal ratio was 1.1:1.

EXAMPLE 7

A 600-ml beaker was charged with 120 g deionized water. The water was stirred vigorously while two solutions (i) 150 g of a ferric nitrate solution (11.78% Fe, 0.316 mole) and (ii) 280 g of chelant solution (37.6% tetrasodium ethylenediamine-N,N'-disuccinate, 0.277 mole; 5.1 % disodium ethylenediamine-N-monosuccinate, 0.064 mole) were simultaneously pumped into it over a period of twenty minutes. The resulting cloudy mixture was warmed at 60° C. for 90 minutes and filtered, removing approximately 1.0 g of insoluble material. 500 g of iron chelate solution was recovered, containing 3.42% Fe by weight.

EXAMPLE 8

A 600-ml beaker was charged with a "heel" of 100 g of previously prepared iron chelate solution (3.4% iron). While this solution was vigorously stirred, two solutions (as in Example 7, except that the ferric nitrate solution was diluted with 120 g water) were simultaneously pumped into it over a period of twenty minutes. The mixture remained a solution throughout the course of the addition. After the addition was complete, the resulting solution was stirred at ambient temperature for another fifteen minutes and filtered, removing only a trace of insoluble material. 632 g of iron chelate solution was recovered, containing 3.34% Fe by weight.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A method for producing a ferric chelate of a polyamino disuccinic acid comprising adding simultaneously to a vessel an alkali metal salt of the polyamino disuccinic acid and a solution of a ferric salt under conditions to produce a stable iron chelate solution wherein the final iron chelate solution is greater than one percent by weight iron.

2. The method of claim 1 wherein the polyamino disuccinic acid has two or more nitrogen atoms wherein two of the nitrogen atoms are bonded to a succinic acid moiety and the polyamino disuccinic acid has from 10 to about 50 carbon atoms which are unsubstituted or substituted with an alkyl group containing 1 to about 12 carbon atoms, or an arylalkyl group containing about 6 to about 12 carbon atoms, or alkylaryl group containing about 6 to about 12 carbon atoms, wherein any of the atoms in the molecule may also be substituted with from 0 to about 12 atoms other than carbon selected from the group consisting of oxygen, sulfur, phosphorus, nitrogen, hydrogen, and various combinations of these elements.

3. The method of claim 2 wherein the polyamino disuccinic acid has from 2 to about 6 nitrogen atoms wherein the nitrogen atoms are separated by alkylene groups of from 1 to about 12 carbon atoms each.

4. The method of claim 2 wherein the polyamino disuccinic acid is selected from ethylenediamine-N,N'-disuccinic acid, diethylenetriamine-N,N"-disuccinic acid, triethylentetraamine-N,N'"-disuccinic acid, 1,6-hexamethylenediamine-N,N'-disuccinic acid, tetraethylenepentamine-N,N""-disuccinic acid, 2-hydroxypropylene-1,3-diamine-N,N'-disuccinic acid, 1,2-propylenediamine-N,N'-disuccinic acid, 1,3-propylenediamine-N,N'-disuccinic acid, cis-cyclohexanediamine-N,N'-disuccinic acid, trans-cyclohexanediamine-N,N'-disuccinic acid, ethylenebis(oxyethylenenitrilo)-N,N'-disuccinic acid, and combinations thereof.

5. The method of claim 3 wherein the polyamino disuccinic acid has only two nitrogen atoms.

6. The method of claim 5 wherein the remaining valence of the two nitrogen atoms of the polyamino disuccinic acid is filled with hydrogen or an alkyl group.

7. The method of claim 6 wherein the remaining valence of the two nitrogen atoms is filled with hydrogen.

8. The method of claim 4 wherein the polyamino disuccinic acid is ethylenediamine-N,N'-disuccinic acid.

9. The method of claim 8 wherein the ethylenediamine-N,N'-disuccinic acid is the S,S isomer.

10. The method of claim 1 wherein the alkali metal is potassium or sodium.

11. The method of claim 10 wherein the alkali metal is potassium.

12. The method of claim 10 wherein the alkali metal is sodium.

13. The method of claim 1 wherein the polyamino disuccinic acid further contains at least one polyamino monosuccinic acid.

14. The method of claim 13 wherein the polyamine substitutent of the polyamino disuccinic acid and polyamino monosuccinic acid are the same.

15. The method of claim 14 wherein the polyamino disuccinic acid is ethylenediamine-N,N'-disuccinic acid and the polyamino monosuccinic acid is ethylenediamine-N-monosuccinic acid.

16. The method of claim 14 wherein the polyamino disuccinic acid and polyamino monosuccinic acid alkali metal salt are produced from the reaction in an aqueous media of a polyamine with maleic anhydride, maleic acid, or fumaric acid and an alkali metal hydroxide.

17. The method of claim 16 wherein the polyamine is ethylenediamine.

18. The method of claim 16 wherein the alkali metal is potassium or sodium.

19. The method of claim 1 wherein the ferric salt is a ferric halide, ferric nitrate, ferric acetate or ferric sulfate.

20. The method of claim 19 wherein the ferric salt is ferric nitrate.

21. The method of claim 1 wherein the molar ratio of the polyamino disuccinic acid to iron in the final solution is about 1 to 1 to about 1.3 to 1.

22. The method of claim 8 wherein the molar ratio of ethylenediamine-N,N'-disuccinic acid to iron in the final solution is about 1 to 1 to about 1.3 to 1.

23. The method of claim 13 wherein the molar ratio of the sum of the polyamino disuccinic acid and polyamino monosuccinic acid to iron in the final iron chelate solution is about 1 to 1 to about 1.3 to 1.

24. The method of claim 23 wherein the polyamino disuccinic acid is ethylenediamine-N,N'-disuccinic acid and the polyamino monosuccinic acid is ethylenediamine-N-monosuccinic acid.

25. The method of claim 24 wherein the ferric salt is a ferric halide, ferric nitrate, ferric acetate or ferric sulfate.

26. The method of claim 25 wherein the ferric salt is ferric nitrate.

27. The method of claim 1 wherein the vessel contains a heel of a previously prepared ferric chelate solution.

28. The method of claim 27 wherein the polyamino disuccinic acid is ethylenediamine-N,N'-disuccinic acid.

29. The method of claim 28 wherein the ethylenediamine-N,N'-disuccinic acid is the S,S isomer.

30. The method of claim 28 wherein the ferric salt is a ferric halide, ferric nitrate, ferric acetate or ferric sulfate.

31. The method of claim 30 wherein the ferric salt is ferric nitrate.

32. The method of claim 13 wherein the vessel contains a heel of a previously prepared ferric chelate solution.

33. The method of claim 32 wherein the polyamino disuccinic acid is ethylenediamine-N,N'-disuccinic acid and the polyamino monosuccinic acid is ethylenediamine-N-monosuccinic acid.

34. The method of claim 33 wherein the ferric salt is a ferric halide, ferric nitrate, ferric acetate or ferric sulfate.

35. The method of claim 34 wherein the ferric salt is ferric nitrate.

* * * * *